US012758169B2

(12) United States Patent
Fan et al.

(10) Patent No.: US 12,758,169 B2
(45) Date of Patent: Oct. 13, 2026

(54) DUAL SOURCE CT MACHINE AND DRUM FOR DUAL SOURCE CT MACHINE

(71) Applicant: Siemens Shanghai Medical Equipment Ltd., Shanghai (CN)

(72) Inventors: Li Mei Fan, Shanghai (CN); Tie Biao Zhu, Shanghai (CN); Jing Ming Zheng, Shanghai (CN)

(73) Assignee: Siemens Shanghai Medical Equipment Ltd., Shanghai (CN)

(*) Notice: Subject to any disclaimer, the term of this patent is extended or adjusted under 35 U.S.C. 154(b) by 122 days.

(21) Appl. No.: 18/869,150

(22) PCT Filed: May 10, 2023

(86) PCT No.: PCT/CN2023/093294
§ 371 (c)(1),
(2) Date: Nov. 25, 2024

(87) PCT Pub. No.: WO2023/231729
PCT Pub. Date: Dec. 7, 2023

(65) Prior Publication Data

US 2025/0345016 A1 Nov. 13, 2025

(30) Foreign Application Priority Data

May 30, 2022 (CN) ......................... 202221397178.0

(51) Int. Cl.

| | |
|---|---|
| ***A61B 6/40*** | (2024.01) |
| ***A61B 6/00*** | (2006.01) |
| ***A61B 6/03*** | (2006.01) |
| *A61B 6/50* | (2024.01) |

(52) U.S. Cl.
CPC ............ *A61B 6/4014* (2013.01); *A61B 6/035* (2013.01); *A61B 6/4435* (2013.01); *A61B 6/56* (2013.01); *A61B 6/503* (2013.01)

(58) Field of Classification Search
CPC ..... A61B 6/4014; A61B 6/035; A61B 6/4435; A61B 6/56; A61B 6/503
See application file for complete search history.

(56) References Cited

U.S. PATENT DOCUMENTS

| | | | | |
|---|---|---|---|---|
| 10,695,586 B2* | 6/2020 | Harper | ................. | A61N 5/1081 |
| 2014/0270051 A1* | 9/2014 | Smithanik | ............ | A61B 6/4435 378/197 |
| 2016/0058398 A1* | 3/2016 | Jensch | .................. | A61B 6/035 378/204 |

OTHER PUBLICATIONS

Schmidt et al, "Principles and applications of dual source CT", 2020, Physica Medica 79(2020) 36-36, pp. 1-11 (Year: 2020).*
Besson GM, "A New CT System Architecture for High Temporal Resolution with Applications to Improved Geometric Dose Efficiency and Sparse Sampling", Progress In Biomedical Optics And Imaging, Spie—International Society For Optical Engineering, Bellingham, WA, US, vol. {0} 9412, Mar. 18, 2015 (Mar. 18, 2015), p. 94120Y-94120Y, XP060050938.
Jul. 19, 2023 (PCT) International Search Report and Written Opinion—App. PCT/CN2023/093294.

* cited by examiner

*Primary Examiner* — Uzma Alam
*Assistant Examiner* — Fani Polyzos Boosalis
(74) *Attorney, Agent, or Firm* — Banner & Witcoff, Ltd.

(57) ABSTRACT

The disclosure discloses a dual source CT machine and a drum therefor. The drum is mounted to an outer rim of a bearing, and an inner rim of the bearing is mounted to a gantry of the dual source CT machine.

10 Claims, 7 Drawing Sheets

DUAL SOURCE CT MACHINE AND DRUM FOR DUAL SOURCE CT MACHINE

CROSS-REFERENCE TO RELATED APPLICATIONS

The present application is a national stage entry of PCT application no. PCT/CN2023/093294, filed May 10, 2023, which claims priority to and the benefit of China patent application no. CN 202221397178.0, filed on May 30, 2022, the contents of each of which are incorporated herein by reference in their entireties.

TECHNICAL FIELD

The disclosure generally relates to the technical field of medical devices and, more specifically, to a dual source CT machine and a drum for a dual source CT machine.

BACKGROUND

A drum is a vital structural component on a CT machine, which needs to support various vital electrical components such as an X-ray tube, a detector, a high voltage generator, a high pressure tank, and a tube cooling system. In a traditional design, one CT machine is equipped with one drum, and for each type of electrical component, one electrical component is mounted to the drum. Therefore, when the CT machine scans once, the drum needs to complete one revolution. For the detection of cardiac organs, the scan needs to be completed in a short period of time. Therefore, the drum is required to have an extremely high rotational speed, and patients need to hold their breath to complete the scan.

In a traditional dual source CT machine, the drum has a cylindrical structure, and a mounting surface of each type of electrical component is on a side wall of the cylinder. Therefore, the side wall is required to have a sufficient height and thickness. Therefore, the drum with the structure has a large external dimension, and has a large weight.

SUMMARY

In view of the above, to eliminate or alleviate the above problems, the disclosure discloses a drum for a dual source CT machine. The dual source CT machine using the drum is particularly suitable for a heart scan, does not require patients to hold their breath during the scan, and can perform high quality imaging for any heart rate condition. The disclosure further discloses a dual source CT machine using the above drum.

In the drum for a dual source CT machine of the disclosure, the drum is mounted to an outer rim of a bearing, and an inner rim of the bearing is mounted to a gantry of the dual source CT machine. The drum includes: a ring-shaped front drum, where the ring-shaped front drum has a first side surface and a second side surface opposite to each other, a first system mounting area configured for a first X-ray tube system to be mounted and a second system mounting area configured for a second X-ray tube system to be mounted are arranged on the first side surface of the front drum, and a front flange extending in an axial direction from an inner ring edge of the front drum is formed on the second side surface of the front drum; and a ring-shaped rear drum, where the rear drum has a first side surface and a second side surface opposite to each other, a first component mounting area configured for a first set of components matching the first X-ray tube system to be mounted and a second component mounting area configured for a second set of components matching the second X-ray tube system to be mounted are arranged on the first side surface of the rear drum, and a rear flange extending in the axial direction from an inner ring edge of the rear drum is formed on the second side surface of the rear drum. The front drum and the rear drum are arranged coaxially, the front flange and the rear flange face each other, the front drum is connected to the bearing through the front flange, and the rear drum is connected to the bearing through the rear flange.

Further, the first system mounting area includes a first tube mounting area configured for a first tube to be mounted and a first detector mounting area configured for a first detector to be mounted, and a first X-ray path is formed between the first tube and the first detector; the second system mounting area includes a second tube mounting area configured for a second tube to be mounted and a second detector mounting area configured for a second detector to be mounted, and a second X-ray path is formed between the second tube and the second detector; and the first X-ray path and the second X-ray path are both perpendicular to the axial direction, and an included angle between the first X-ray path and the second X-ray path is between 45 degrees and 135 degrees.

Further, the front drum includes at least one front protrusion protruding from the first side surface of the front drum, and the at least one front protrusion is arranged around and in contact with at least one X-ray tube system of the first X-ray tube system and the second X-ray tube system; and/or the rear drum includes at least one rear protrusion protruding from the first side surface of the rear drum, and the at least one rear protrusion is arranged around and in contact with at least one set of components of the first set of components and the second set of components.

Further, at least one of the at least one front protrusion is arranged on a radial outer side of the at least one X-ray tube system; and/or at least one of the at least one rear protrusion is arranged on a radial outer side of the at least one set of components.

Further, each of the first tube mounting area and the second tube mounting area has a through hole, so that the first tube mounted in the first tube mounting area and the second tube mounted in the second tube mounting area pass through the corresponding through holes and are mounted to the front drum.

Further, a balance weight is mounted at a position on the second side surface of the front drum staggered from the first system mounting area and the second system mounting area located on the first side surface of the front drum.

Further, one or more grooves are arranged on circumferential surfaces of inner holes of the front drum and the rear drum, and the first X-ray tube system and the second X-ray tube system are respectively connected to the first set of components and the second set of components through cables extending through the one or more grooves.

Further, each of the first component mounting area and the second component mounting area includes a high voltage generator mounting area configured for a high voltage generator to be mounted, a high pressure tank mounting area configured for a high pressure tank to be mounted, and a tube cooling system mounting area configured for a tube cooling system to be mounted, and the first component mounting area and the second component mounting area are arranged symmetrically with respect to a center of the rear drum.

Further, a heat sink and/or a heat dissipation hole is arranged on the front drum and/or the rear drum.

Further, a balance weight is mounted at a position on the second side surface of the rear drum staggered from the first component mounting area and the second component mounting area located on the first side surface of the rear drum.

According to another aspect of the disclosure, a dual source CT machine includes the above drum.

Through the drum of the disclosure and the dual source CT machine including the drum, the scan time of the CT machine can be reduced, the scan efficiency can be improved, and clearer scanned images can be obtained. In addition, the drum of the disclosure has a light weight and low costs, is integrated with many functions, and has a more optimized structure.

BRIEF DESCRIPTION OF THE DRAWINGS

Embodiments of the disclosure are described in detail below with reference to the drawings, so as to make a person of ordinary skill in the art be more aware of the above and other features and advantages of the disclosure.

In the figures.

REFERENCE NUMERALS

Figure 1:
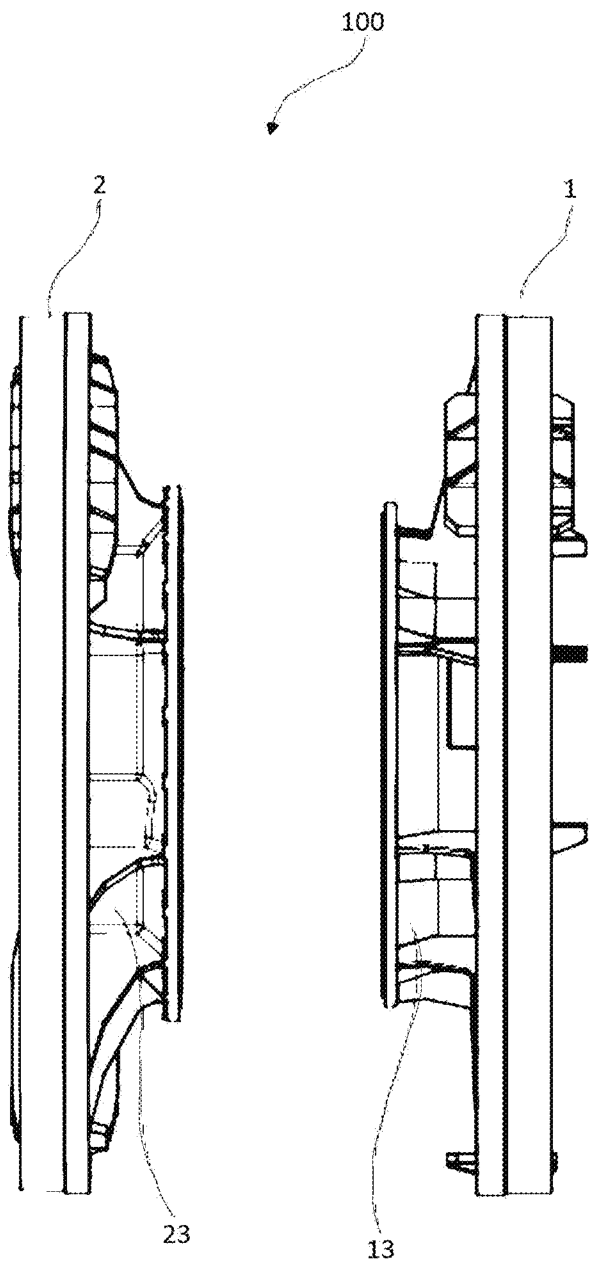
FIG. 1 shows a drum for a dual source CT machine according to an embodiment of the disclosure.

100 Drum
1 Front drum
1*a* First side surface of front drum
1*b* Second side surface of front drum
1*c* Side end surface of front drum
10 Front protrusion
11 First system mounting area
111 First tube mounting area
112 First detector mounting area
12 Second system mounting area
121 Second tube mounting area
122 Second detector mounting area
13 Front flange
2 Rear drum
2*a* First side surface of rear drum
2*b* Second side surface of rear drum
2*c* Side end surface of rear drum
20 Rear protrusion
21 First component mounting area
211 High voltage generator mounting area
212 High pressure tank mounting area
213 tube cooling system mounting area
22 Second component mounting area
221 High voltage generator mounting area
222 High pressure tank mounting area
223 Tube cooling system mounting area
23 Rear flange
R1 First X-ray path
R2 Second X-ray path
a Included angle
G1 Groove on front drum
G2 Groove on rear drum
P1 Balance weight mounting position on front drum
P2 Balance weight mounting position on rear drum

DETAILED DESCRIPTION

In order to make the purposes, technical solutions, and advantages of the disclosure clearer, the following embodiments are provided to describe the disclosure in further detail.

Referring to FIG. 1 to FIG. 7, the disclosure provides a drum 100 for a dual source CT machine. The drum 100 is mounted to an outer rim of a bearing, and an inner rim of the bearing is mounted to a gantry of the dual source CT machine. Generally, the drum 100 may include a ring-shaped front drum 1 and a ring-shaped rear drum 2. The front drum 1 and the rear drum 2 both may be made by casting aluminum. Such a casting has materials with a small weight and high strength.

Figure 2:
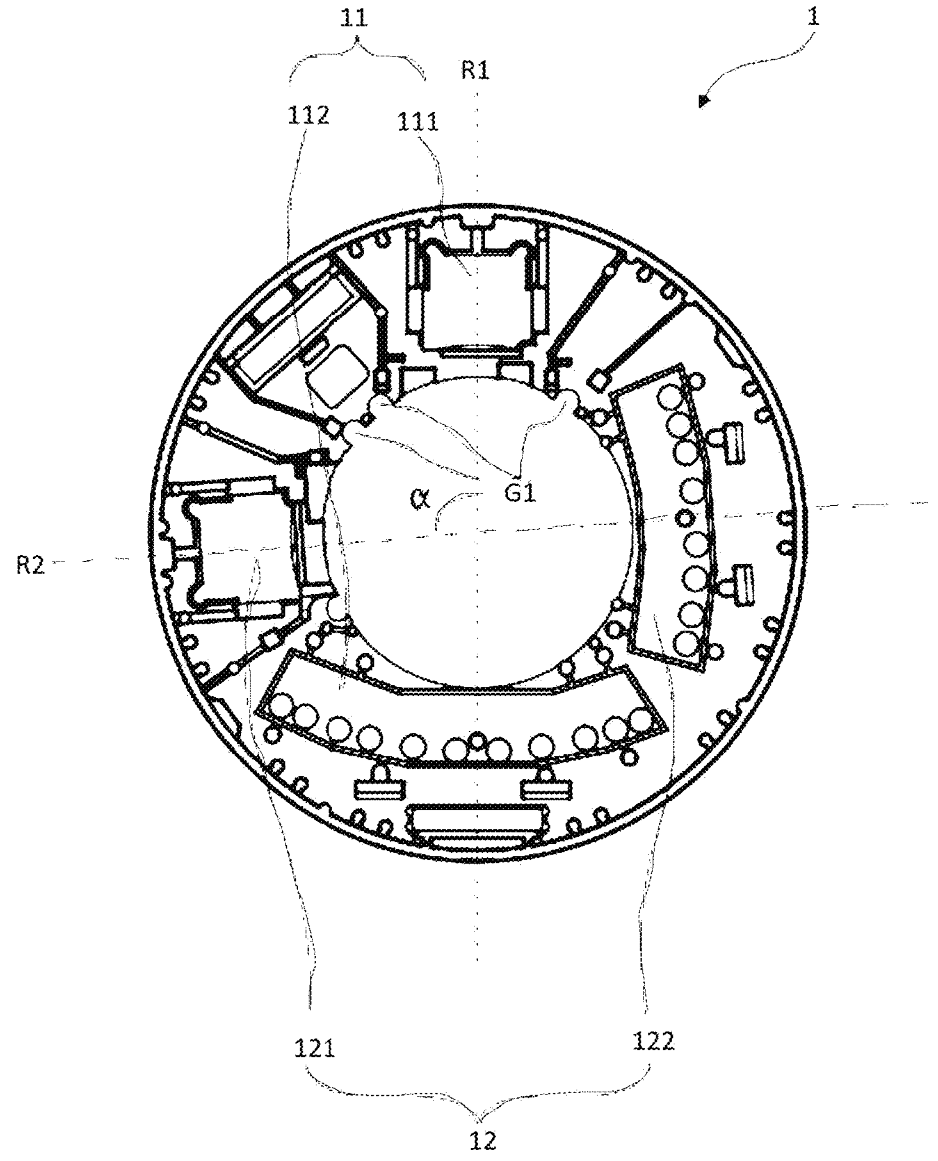
FIG. 2 is a side view showing a front drum of the drum in FIG. 1.
Figure 3:
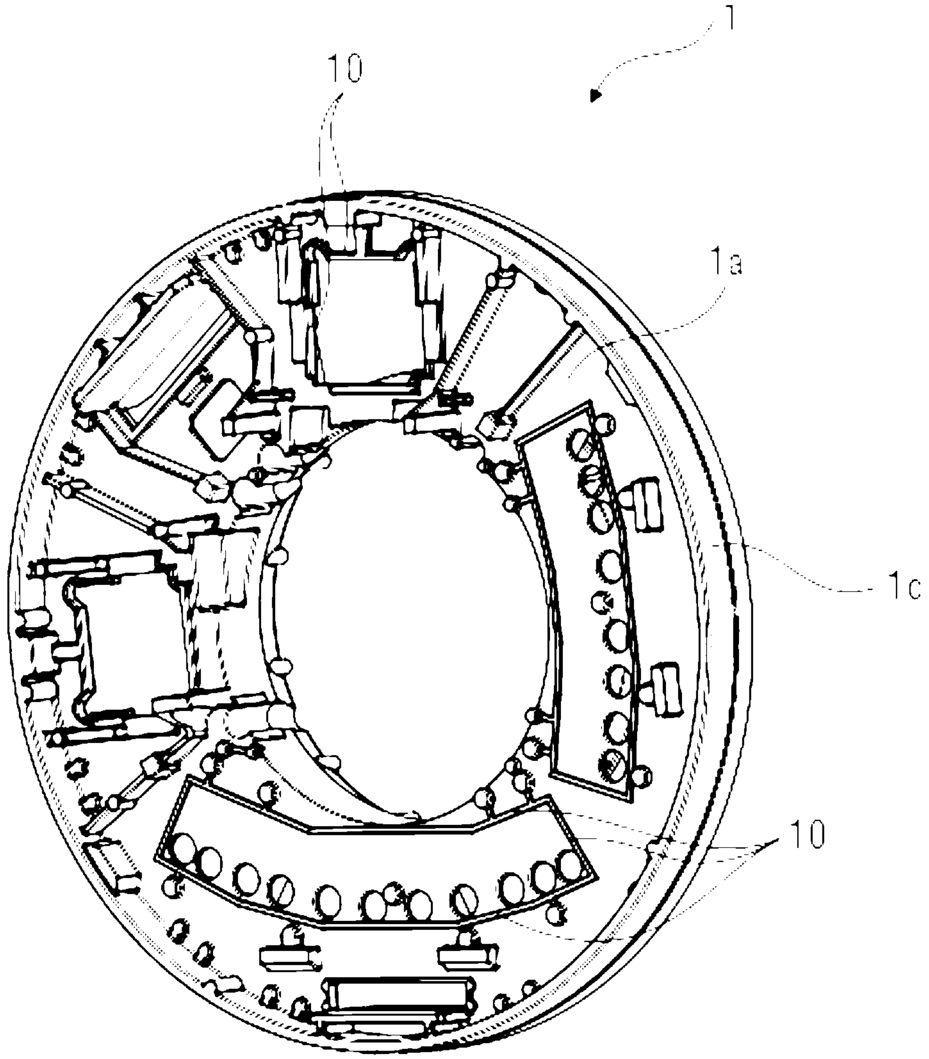
FIG. 3 is a three-dimensional view showing the front drum of the drum in FIG. 1, showing a first side of the front drum.
Figure 4:
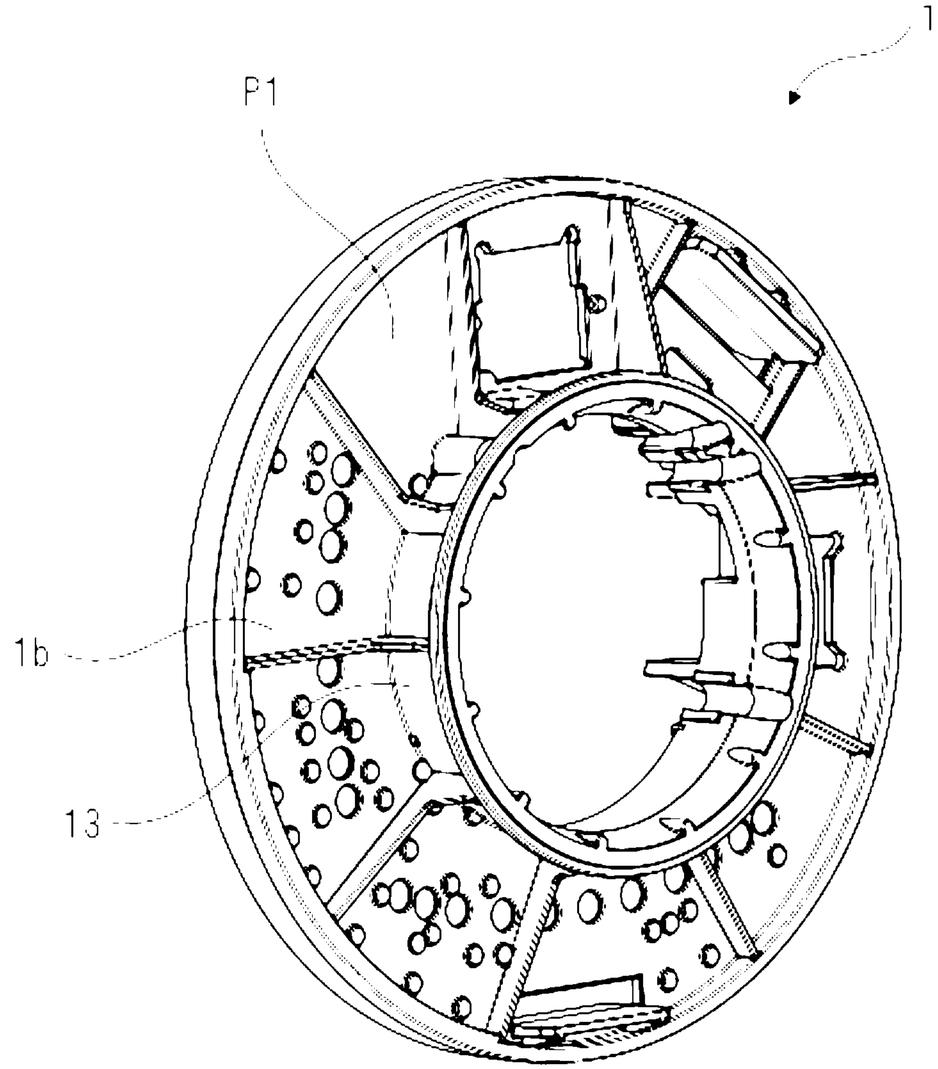
FIG. 4 is a three-dimensional view showing the front drum of the drum in FIG. 1 from another perspective, showing a second side of the front drum.

Specifically, referring to FIG. 2 to FIG. 4, the front drum 1 has a first side surface 1*a* and a second side surface 1*b* opposite to each other. A first system mounting area 11 configured for a first X-ray tube system to be mounted and a second system mounting area 12 configured for a second X-ray tube system to be mounted are arranged on the first side surface 1*a* of the front drum 1. A front flange 13 extending in an axial direction (the axial direction herein is an axial direction of the drum, and since the drum includes the front drum 1 and the rear drum 2 arranged coaxially, the axial direction of the drum, in fact, an axial direction of the front drum, and an axial direction of the rear drum are the same) from an inner ring edge of the front drum 1 is formed on the second side surface 1*b* of the front drum 1.

Figure 5:
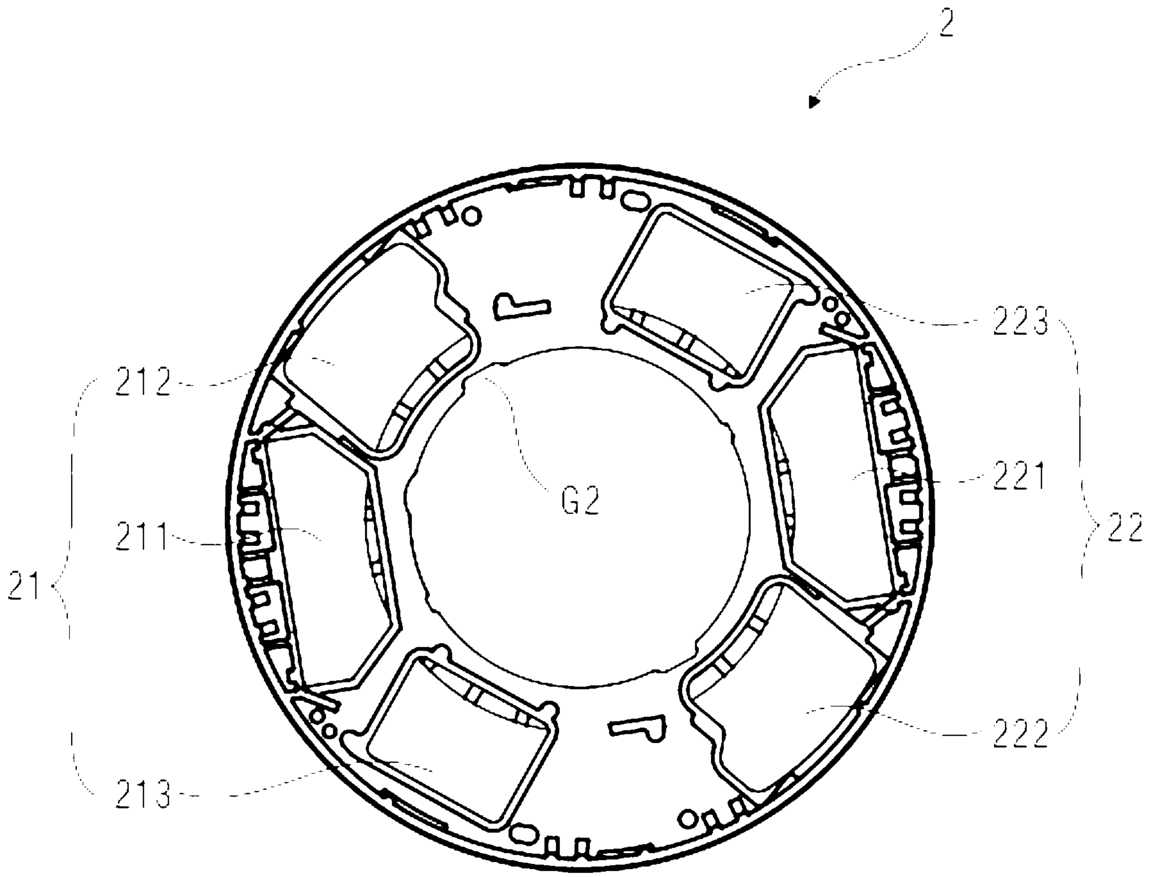
FIG. 5 is a side view showing a rear drum of the drum in FIG. 1.
Figure 6:
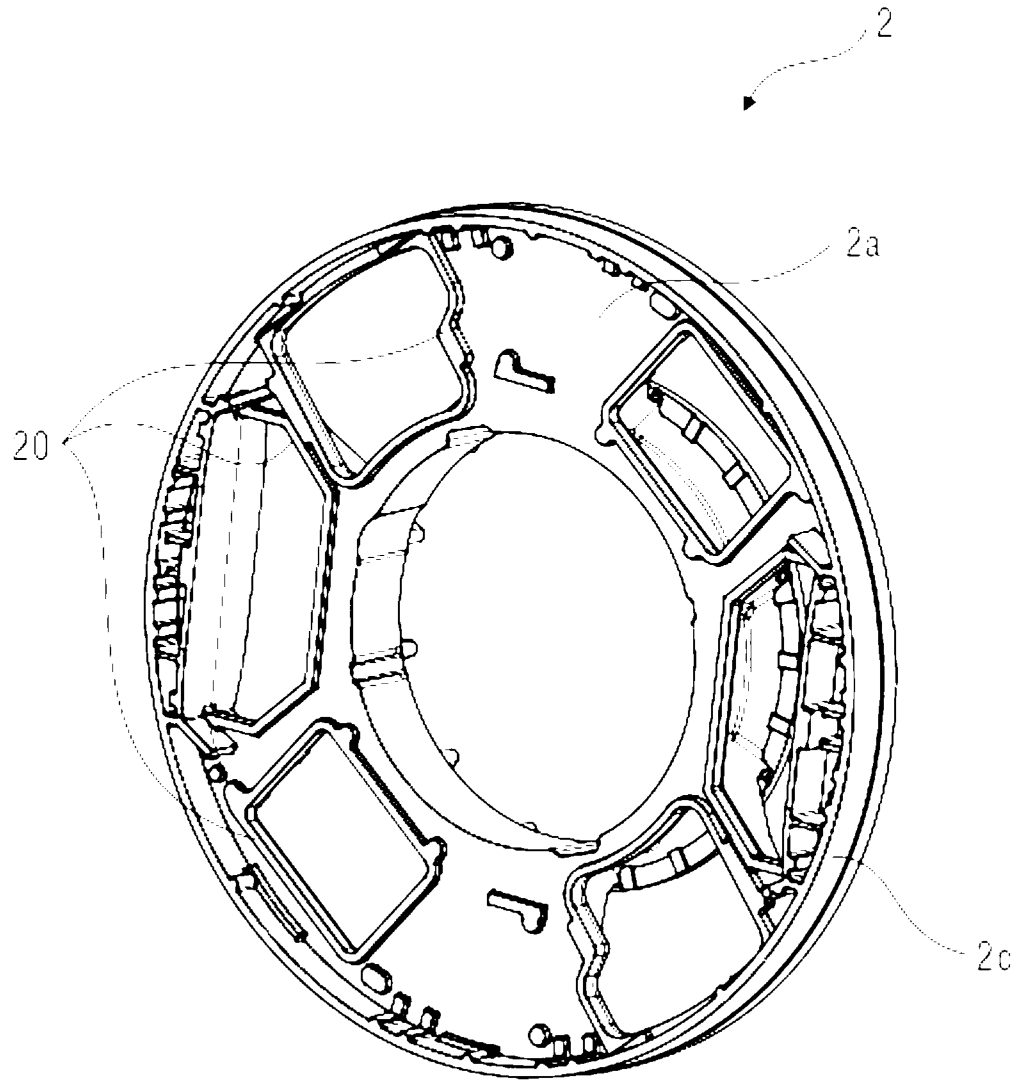
FIG. 6 is a three-dimensional view showing the rear drum of the drum in FIG. 1, showing a first side of the rear drum.
Figure 7:
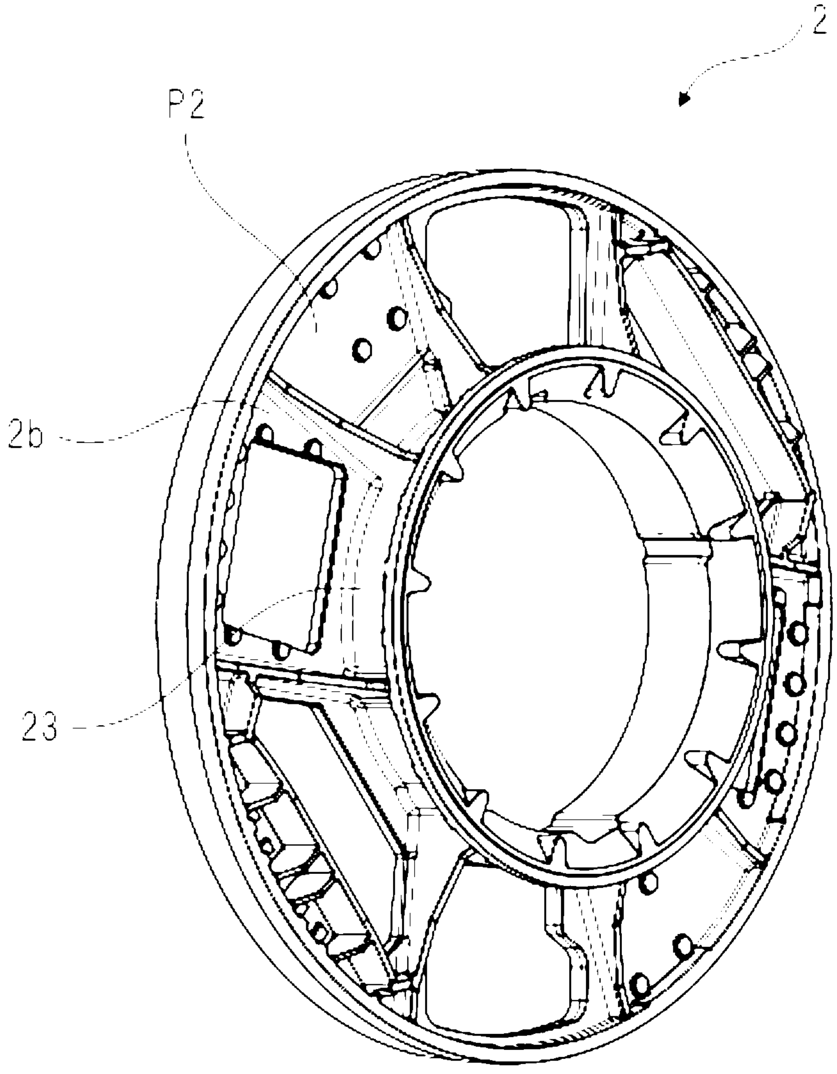
FIG. 7 is a three-dimensional view showing the rear drum of the drum in FIG. 1 from another perspective, showing a rear side of the rear drum.

Specifically, referring to FIG. 5 to FIG. 7, the rear drum 2 has a first side surface 2*a* and a second side surface 2*b* opposite to each other. A first component mounting area 21 configured for a first set of components matching the first X-ray tube system to be mounted and a second component mounting area 22 configured for a second set of components matching the second X-ray tube system to be mounted are arranged on the first side surface 2*a* of the rear drum 2. A rear flange 23 extending in the axial direction from an inner ring edge of the rear drum 2 is formed on the second side surface 2*b* of the rear drum 2.

The front drum 1 and the rear drum 2 are arranged coaxially, and the front flange 13 and the rear flange 23 face each other. The front drum 1 is connected to the bearing through the front flange 13, and the rear drum 2 is connected to the same bearing through the rear flange 23. Specifically, the front flange 13 and the rear flange 23 may be connected to the bearing through bolts, for example.

Referring to FIG. 2, the first system mounting area 11 includes a first tube mounting area 111 configured for a first tube to be mounted and a first detector mounting area 112 configured for a first detector to be mounted. A first X-ray path R1 is formed between the first tube and the first detector. The first tube and the first detector are not shown in the figure, and only the first X-ray path R1 is schematically shown with a broken line. The second system mounting area 12 includes a second tube mounting area 121 configured for a second tube to be mounted and a second detector mounting area 122 configured for a second detector to be mounted. A second X-ray path R2 is formed between the second tube and the second detector. The second tube and the second detector are not shown in the figure, and only the second X-ray path R2 is schematically shown with a broken line. The first X-ray path R1 and the second X-ray path R2 are both perpendicular to the axial direction (that is, in a radial direction of the drum), and an included angle α between the first X-ray path R1 and the second X-ray path R2 is between 45 degrees and 135 degrees. The included angle α may be for instance 90 degrees.

Referring to FIG. 3, the front drum 1 may include at least one front protrusion 10 protruding from the first side surface 1*a* of the front drum 1. The at least one front protrusion 10 is arranged around and in contact with at least one X-ray tube system of the first X-ray tube system and the second X-ray tube system. Similarly, referring to FIG. 6, the rear drum 2 may include at least one rear protrusion 20 protruding from the first side surface 2*a* of the rear drum 2. The at least one rear protrusion 20 is arranged around and in contact with at least one set of components of the first set of components and the second set of components. Specifically, at least one of the at least one front protrusion 10 is arranged on a radial outer side of the at least one X-ray tube system; and/or at least one of the at least one rear protrusion 20 is arranged on a radial outer side of the at least one set of components. When the front drum 1 and the rear drum 2 rotate at a high speed, the electrical components mounted thereto bear an enormous centrifugal force. Through the arrangement of the front protrusion 10 and the rear protrusion 20, not only the centrifugal force on the electrical components can be born, but also the rigidity of the casting can be increased. In this way, the centrifugal force is converted to the casting material, thereby significantly improving the safety.

Referring to FIG. 2 to FIG. 4, each of the first tube mounting area 111 and the second tube mounting area 121 may have a through hole, so that the first tube mounted in the first tube mounting area 111 and the second tube mounted in the second tube mounting area 121 pass through the corresponding through holes and are mounted to the front drum 1. In this way, a part of the first tube is located on a first side of the front drum 1, and the other part is located on a second side of the front drum 1, and a part of the second tube is located on the first side of the front drum 1 and the other part is located on the second side of the front drum 1, thereby facilitating the structural balance.

Referring to FIG. 3, a data transmission system may be mounted to a side end surface 1*c* of the front drum 1 for data transmission with the electrical components. Referring to FIG. 4, a balance weight (not shown) may be mounted at a position P1 on the second side surface 1*b* of the front drum 1 staggered from the first system mounting area 11 and the second system mounting area 12 located on the first side surface 1*a* of the front drum 1, thereby facilitating the structural balance.

Referring to FIG. 2 and FIG. 5, one or more grooves G1, G2 may arranged on circumferential surfaces of inner holes of the front drum 1 and the rear drum 2, and the first X-ray tube system and the second X-ray tube system (not shown) may be respectively connected to the first set of components and the second set of components through cables extending through the one or more grooves G1, G2.

Referring to FIG. 5, each of the first component mounting area 21 and the second component mounting area 22 includes a high voltage generator mounting area 211, 221 configured for a high voltage generator to be mounted, a high pressure tank mounting area 212, 222 configured for a high pressure tank to be mounted, and a tube cooling system mounting area 213, 223 configured for a tube cooling system to be mounted, and the first component mounting area 21 and the second component mounting area 22 are arranged symmetrically with respect to a center of the rear drum 2. In this way, self-balance can be realized. Therefore, only a weight distribution of the drum and weight differences between the components need to be balanced and adjusted, thereby reducing the weight of the balance weight and reducing the balance adjustment time.

Referring to FIG. 2 to FIG. 7, due to the high power and the large amount of heat of the electrical components, a heat sink and/or a heat dissipation hole may be arranged on the front drum 1 and/or the rear drum 2, such as a heat dissipation hole in the first detector mounting area 112 or the second detector mounting area 122 extending through the front drum 1. The heat dissipation hole is usually arranged near electrical components on the drum that generate a large amount of heat. In addition, the drum casting may be designed as a thin-walled frame structure to facilitate heat dissipation.

Referring to FIG. 6, a slip ring system may be mounted to a side end surface 2*c* of the rear drum 2 for transmitting power and signals. Referring to FIG. 7, a balance weight (not shown) is mounted at a position (P2) on the second side surface 2*b* of the rear drum 2 staggered from the first component mounting area 21 and the second component mounting area 22 located on the first side surface 2*a* of the rear drum 2.

Referring to FIG. 4 and FIG. 7, the front drum 1 may include a plurality of support ribs connected between the second side surface 1*b* of the front drum 1 and the front flange 13 and spaced apart in a circumferential direction. Similarly, the rear drum 2 may also include a plurality of support ribs connected between the second side surface 2*b* of the rear drum 2 and the rear flange 23 and spaced apart in the circumferential direction. The arrangement of the support ribs increases the structural stability of the front drum 1 and the rear drum.

A dual source CT machine of the disclosure includes the drum in the above embodiment. The front drum and the rear drum of the drum are mounted to an outer rim of a bearing of the CT machine, and an inner rim of the bearing is mounted to a gantry of the CT machine.

Through the drum of the disclosure including the front drum 1 and the rear drum 2, the scan time of the CT machine can be reduced, the scan efficiency can be improved, and clearer scanned images can be obtained. The drum of the disclosure has a light weight and low costs, is integrated with many functions, and has a more optimized structure.

The above descriptions are example embodiments of the disclosure, and are not intended to limit the disclosure. Any modification, equivalent replacement, improvement, or the like made within the spirit and principle of the disclosure should fall within the protection scope of the disclosure.

The invention claimed is:

1. A drum for a dual source CT machine, the drum being mounted to an outer rim of a bearing, and an inner rim of the bearing being mounted to a gantry of the dual source CT machine, the drum comprising:

a ring-shaped front drum comprising:

a first side surface and a second side surface opposite to one other;

a first system mounting area configured for a first X-ray tube system to be mounted;

a second system mounting area configured for a second X-ray tube system to be mounted, wherein the first system mounting area and the second system mounting area are arranged on the first side surface of the ring-shaped front drum; and a front flange extending in an axial direction from an inner ring edge of the ring-shaped front drum, wherein the front flange is formed on the second side surface of the ring-shaped front drum; and a ring-shaped rear drum comprising:

a third side surface and a fourth side surface opposite to one other;

a first component mounting area configured for a first set of components matching the first X-ray tube system to be mounted; and a second component mounting area configured for a second set of components matching the second X-ray tube system to be mounted, wherein the first component mounting area and the second component mounting area are arranged on the third side surface of the ring-shaped rear drum; and a rear flange extending in the axial direction from an inner ring edge of the ring-shaped rear drum, and wherein the rear flange is formed on the fourth side surface of the ring-shaped rear drum, wherein the ring-shaped front drum and the ring-shaped rear drum are arranged coaxially, wherein the front flange and the rear flange face one other, wherein the ring-shaped front drum is connected to the bearing via the front flange, and wherein the ring-shaped rear drum is connected to the bearing via the rear flange.

2. The drum according to claim 1, wherein the first system mounting area comprises:

a first tube mounting area configured for a first tube to be mounted; and a first detector mounting area configured for a first detector to be mounted, wherein a first X-ray path is formed between the first tube and the first detector, and wherein the second system mounting area comprises:

a second tube mounting area configured for a second tube to be mounted; and a second detector mounting area configured for a second detector to be mounted, wherein a second X-ray path is formed between the second tube and the second detector, wherein the first X-ray path and the second X-ray path are each perpendicular to the axial direction, and wherein an angle between the first X-ray path and the second X-ray path is between 45 degrees and 135 degrees.

3. The drum according to claim 2, wherein each of the first tube mounting area and the second tube mounting area has a respective through hole such that the first tube mounted in the first tube mounting area and the second tube mounted in the second tube mounting area pass through the through holes of the first tube mounting area and the second tube mounting area, respectively, and are mounted to the ring-shaped front drum.

4. The drum according to claim 1, wherein:

the ring-shaped front drum comprises at least one front protrusion protruding from the first side surface, the at least one front protrusion is arranged around and in contact with at least one X-ray tube system of the first X-ray tube system and the second X-ray tube system; and/or the ring-shaped rear drum comprises at least one rear protrusion protruding from the third side surface, and the at least one rear protrusion is arranged around and in contact with at least one set of components of the first set of components and the second set of components.

5. The drum according to claim 4, wherein the at least one front protrusion is arranged on a radial outer side of the at least one X-ray tube system.

6. The drum according to claim 4, wherein the at least one rear protrusion is arranged on a radial outer side of the at least one set of components.

7. The drum according to claim 1, wherein a balance weight is mounted at a position on the second side surface of the ring-shaped front drum staggered from the first system mounting area and the second system mounting area located on the first side surface.

8. The drum according to claim 1, wherein one or more grooves are arranged on circumferential surfaces of inner holes of the ring-shaped front drum and the ring-shaped rear drum, and wherein the first X-ray tube system and the second X-ray tube system are respectively connected to the first set of components and the second set of components via cables extending through the one or more grooves.

9. The drum according to claim 1, wherein each of the first component mounting area and the second component mounting area comprises:

a high voltage generator mounting area configured for a high voltage generator to be mounted;

a high pressure tank mounting area configured for a high pressure tank to be mounted; and a tube cooling system mounting area configured for a tube cooling system to be mounted, wherein the first component mounting area and the second component mounting area are arranged symmetrically with respect to a center of the ring-shaped rear drum.

10. The drum according to claim 1, wherein a balance weight is mounted at a position on the fourth side surface of the ring-shaped rear drum staggered from the first component mounting area and the second component mounting area located on the third side surface.

* * * * *